(12) United States Patent
Duez et al.

(10) Patent No.: US 10,473,657 B2
(45) Date of Patent: Nov. 12, 2019

(54) MALARIA DETECTION

(71) Applicant: Magnetrap, Mons (BE)

(72) Inventors: Pierre Duez, Mont-Saint-Guibert (BE); Alain Roch, Mont-Saint-Guibert (BE); Bertrand Blankert, Mont-Saint-Guibert (BE); Phillippe Okusa, Mont-Saint-Guibert (BE); Richard Avaert, Mont-Saint-Guibert (BE)

(73) Assignee: Magnetrap, Mons (BE)

( * ) Notice: Subject to any disclaimer, the term of this patent is extended or adjusted under 35 U.S.C. 154(b) by 0 days.

(21) Appl. No.: 15/521,993

(22) PCT Filed: Oct. 29, 2015

(86) PCT No.: PCT/EP2015/075144
§ 371 (c)(1),
(2) Date: Apr. 26, 2017

(87) PCT Pub. No.: WO2016/066754
PCT Pub. Date: May 6, 2016

(65) Prior Publication Data
US 2017/0336408 A1    Nov. 23, 2017

(30) Foreign Application Priority Data
Oct. 29, 2014    (GB) .................................. 1419230.6

(51) Int. Cl.
*G06T 7/00* (2017.01)
*G01N 33/569* (2006.01)
*G01N 33/72* (2006.01)
*G01N 21/552* (2014.01)
*G01N 33/49* (2006.01)
*G01J 3/44* (2006.01)

(52) U.S. Cl.
CPC ..... *G01N 33/56905* (2013.01); *G01N 21/553* (2013.01); *G01N 33/49* (2013.01); *G01N 33/72* (2013.01); *G01J 3/4406* (2013.01); *G01N 2333/445* (2013.01); *G06T 2207/30024* (2013.01); *Y02A 50/58* (2018.01)

(58) Field of Classification Search
None
See application file for complete search history.

(56) References Cited

U.S. PATENT DOCUMENTS

2012/0257199 A1    10/2012    Liu et al.

FOREIGN PATENT DOCUMENTS

| WO | WO 1992/14149 | 8/1992 | |
| WO | WO-9214149 A1 * | 8/1992 | ........... G01N 33/531 |
| WO | WO 2008/056171 | 5/2008 | |
| WO | WO 2011/100066 | 8/2011 | |

OTHER PUBLICATIONS

International Search Report and Written Opinion dated Jan. 19, 2016, in connection with International Application No. PCT/EP2015/075144, Applicant Universitéde Mons, (10 pages).

(Continued)

*Primary Examiner* — Delomia L Gilliard
(74) *Attorney, Agent, or Firm* — McCracken & Gillen LLC

(57) ABSTRACT

The presence of hemozoin as an indicator of malaria in a blood sample is detected by magnetic separation, dissolution and spectroscopic analysis.

14 Claims, 4 Drawing Sheets

(56) References Cited

OTHER PUBLICATIONS

Office Action issued in connection with Colombian Patent Application No. NC2017/0004272, Applicant UniversitéDe Mons et al., with machine translation (20 pages).
Search Report dated Jul. 10, 2018, in connection with Chinese Patent Application No. 2015800626592 (4 pages).
English Translation of Text of the First Office Action issued in connection with Chinese Patent Application No. 2015800626592 (6 pages).
Kim et al, "Improved Methods for Magnetic Purification of Malaria Parasites and Haemozoin," Malaria Journal 2010, vol. 9:17 (5 pages).
Sullivan, Jr. et al., "On the Molecular Mechanism of Chloroquine's Antimalarial Action," Proceedings of the National Academy of Sciences, USA, Oct. 1996, vol. 93, pp. 11865-11870 (6 pages).
Fairlamb et al., "A Simple Magnetic Method for the Purification of Malarial Pigment," Molecular and Biochemical Parasitology, vol. 12 (1984) pp. 307-312 (6 pages).
Hackett et al., "Magnetic Susceptibility of Iron in Malaria-Infected Red Blood Cells," Biochimica et Biophysica Acta, vol. 1792, (2009) pp. 93-99 (7 pages).
Nam et al., "Magnetic Separation of Malaria-Infected Red Blood Cells in Various Developmental Stages," Analytical Chemistry, 2013, vol. 85, pp. 7316-7323 (8 pages).
Men et al., "A Simple and Inexpensive Haemozoin-Based Colorimetric Method to Evaluate Anti-Malarial Drug Activity," Malaria Journal 2012, vol. 11:272 (5 pages).

* cited by examiner

MALARIA DETECTION

The present invention relates to devices and methods for detection in a sample of a target material having magnetic properties, notably detection of hemozoin in whole blood or tissues as an indication of malarial infection.

Early and accurate diagnosis of malaria is essential for effective disease management and malaria surveillance. Lack of easy, affordable and accurate diagnostic methods has led to the common precaution of "fever equals malaria unless proven otherwise". This leads to over-assumption of malaria, mismanagement of non-malarial fevers, wastage of limited resources and contributes to drug resistance.

Accurate detection and quantification of malarial infection by microscopic examination of thick and thin blood smears is highly dependent on the training and skill of the operator; it also requires equipment and working conditions which are not always available, particularly in rural environments. Rapid diagnostic tests (RDTs) based on antigen-antibody reactions require less skill and equipment but are generally expensive and lack sufficient sensitivity for detection of low-level malaria. Other proposed detection systems have not been found suitable in practice for widespread use in field conditions. For example, US 2012/0257199 A1 discloses adsorption of β-hematin on the surface of magnetic nanoparticles in suspension in a sample and the use of magnetic field enrichment on the sample to increase the signal obtained in Raman spectroscopy whilst WO 2008/056171 A2 discloses the use of a differential absorptive signal to p and s polarized light of β-hematin in blood subjected to a magnetic field of varying intensities.

Therefore there is still a need for improved methods and devices for detecting the presence of malarial infection.

According to one aspect, the present invention provides a method of detecting a target material in a form having magnetic properties in a sample as defined in claim 1. Other aspects are defined in other independent claims. The dependent claims define preferred or alternative embodiments.

The target material in a form having magnetic properties may be an organic magnetic material; it may be hemozoin or β-hematin.

Hemozoin is a by-product formed from the digestion of blood by some blood-feeding parasites. These hematophagous organisms such as malaria parasites digest hemoglobin and release high quantities of free heme, which is the non-protein component of hemoglobin. A heme is a prosthetic group that consists of an iron atom contained in the center of a heterocyclic porphyrin ring. Free heme is toxic to cells, so the parasites convert it into an insoluble crystalline form called hemozoin. Since, at given stages of the parasites cycle, there is a correlation between the concentration of hemozoin in blood and the level of parasitemia, an accurate and sensitive quantification of hemozoin in a blood sample allows detection of malaria at low levels or early stages of the infection.

β-hematin is a synthetic material analogous to hemozoin. β-hematin exhibits similar properties to hemozoin, including spectroscopic and magnetic properties, and may be used to simulate the behaviour of hemozoin.

The method may be used to detect or quantify, and/or capable of detecting or quantifying, a concentration of hemozoin or β-hematin in the sample which is ≤0.12 μg/mL, preferably ≤0.10 μg/mL, more preferably ≤0.08 μg/mL and even more preferably ≤0.06 μg/mL or ≤0.05 μg/mL and/or which is between one of these concentrations and a concentration of 2 μg/mL or 2.5 μg/mL. Detection of a concentration of hemozoin of 0.12 μg/mL allows a detection of parasitemia of 200 parasites per μL (as recommended by the World Health Organisation) whilst detection of a concentration of hemozoin of 0.05 μg/mL allows a detection of parasitemia of 80 parasites per μL. These levels of sensitivity, particularly the lower levels, allow early detection of malaria greatly facilitating patient treatment.

The volume of the sample used for the analysis may be ≤1 mL, preferably ≤750 μL, more preferably ≤500 μL, and even more preferably ≤300 μL. Thus only a very small sample of blood needs to be taken from a person to be tested. Particularly in a microflow system, the volume of the sample used for the analysis may be between 10 μL and 50 μL. The sample for analysis may be collected by venipuncture or finger stick. The volume of blood collected from a prick of blood may be sufficient for the analysis.

The duration of the analysis of the sample (for example from injection of the sample to the reception of final data) may be of no more than 10 minutes, preferably of no more than 8 minutes; more preferably of no more than 6 minutes or no more than 5 minutes. This provides a result significantly more quickly than microscopy.

The sample may comprise an aqueous or organic solvent solution and/or suspension. The sample may comprise a biological matrix or an aqueous or organic solvent solution and/or suspension derived from a biological matrix. The biological matrix may comprise fluids, cells, tissues, extracts, lysates, prokaryote or eukaryote culture cells, supernatants and/or lysates, dialysis samples, microdialysis samples. The sample may comprise human and animal body fluids or tissues, for example whole blood, lysed whole blood, serum, plasma, urine, sperm, erythrocytes and/or leukocytes suspensions or lysates, dissociated and/or lysed tissues, biopsy samples, hairs, nails.

During maturation of malaria, when there is a high concentration of schizonts in red cells, there is a natural lysis of the cells and the hemozoin will be liberated into the blood at the same time as schizonts which will infect new red cells. One advantage of using a sample comprising whole blood (or lysed whole blood) instead of separated or purified red cells is that this allows analysis of the total hemozoin present, including (i) hemozoin which is still within red blood cells; (ii) hemozoin that has previously been released from red blood cells; and (iii) hemozoin that has been incorporated, generally at high levels, in macrophages, monocytes and leukocytes.

The sample preferably comprises lysed whole blood. Any lysis solution used preferentially has a neutral pH or is slightly acidic; this avoids dissolution of hemozoin or β-hematin in the whole blood sample. For example, a whole blood sample may be lysed with a Tris-buffered solution (pH 7), Triton X-100 and saponin. The lysis solution can be prepared following the method described in "Simple and Inexpensive Fluorescence-Based Technique for High-Throughput Antimalarial Drug Screening" (M. Smikstein et al., Antimicrob. Agents Chemother., 2004, vol. 48, p 1803). Other possible lysis solutions include hypotonic buffers of varying pH, preferably acid or neutral. DNase can be added to samples (typically 10-100 μg/mL) along with RNase (10-100 μg/mL) to reduce the viscosity due to the release of nucleic acid material. Nuclease and/or protease inhibitors can be added to all samples undergoing lysis. Possible lysing methods include: mechanical disruption, possibly using glass beads, liquid homogenization, freeze-thaw, mortar and pestle; all methods can be applied with or without sonication. Preferably, the sample comprises whole blood which has been lysed using a lysis solution, that is to say chemically lysed, and which has not been mechanically lysed; this simplifies preparation of the sample.

Before magnetic separation of the target material from the sample, the sample may be purified. Such purification may include filtering, centrifugation, precipitation, direct-phase, reverse-phase, ionic, hydrophilic, affinity, gel-permeation or size-exclusion chromatography or electrophoresis, all combinable with liquid-liquid or solid-phase extraction. Preferably however, no such purification is required or carried out.

The sample to be analysed may be introduced into a carrier fluid which may comprise water, an organic solution, an aqueous solution, for example an aqueous sodium chloride (NaCl) solution notably having a concentration greater than or equal to about 0.3%, 0.6% or 0.9%. Preferably the carrier fluid is water, notably purified water. This provides simplification.

Following magnetic separation, the target material may be collected for analysis by a collecting fluid. The collecting fluid preferably comprises a component in which the separated target material is dissolved to provide an analysable solution. The dissolved target material is preferably in an un-magnetised form, i.e. dissolution results in the loss of the magnetic properties. The collecting fluid may comprise an aqueous solution comprising an alkalinizing agent such as calcium hydroxide, magnesium hydroxide, sodium hydroxide, ammonium hydroxide, organic quaternary ammonium hydroxides, ammonia, organic amines. A preferred collecting fluid is sodium hydroxide solution. The collecting fluid may have a concentration which is greater than or equal to 0.1 M and/or less than or equal to 1 M; a 0.4 M NaOH solution may for example be used. Such solutions are readily available, require only standard laboratory precautions for use and have concentrations which avoid the risk of creating precipitations of salts which could block the apparatus, notably portions of the apparatus having small cross sections, for example any switch valves.

The carrier and/or collecting fluid may comprise one or more additives, for example:
- antioxidants, for example tocopherols, tocotriénols, ascorbic or erythorbic acids or salts, synthetic antioxidants, including butylated hydroxytoluene and butylated hydroxyanisole, or natural phenolic constituents, including flavanones, flavonols, monophenols (thymol, carvacrol, eugenol . . . ) from essential oils, caffeic and ferulic acids, flavonoids and procyanidins from grape and red wine, rosmarine diterpenic acids, olive oil hydroxytyrosol, lignin degradation products and lignanes, reductones which may be adapted to reduce corrosion of internal parts of the device, notably metal microspheres when used; citric, phosphoric or fumaric acid or metal chelatants can also be added to potentialise the antioxidant effect;
- surfactants, for example combined or non-combined non-ionic surfactants (cetomacrogol 1000, cetostearyl alcohol, cetyl alcohol, cocamide dea, cocamide mea, igepal ca-630, isoceteth-20, lauryl glucoside, monolaurin, narrow range ethoxylate, nonidet p-40, nonoxynol-9, nonoxynols, np-40, octaethylene glycol monododecyl ether, n-octyl beta-d-thioglucopyranoside, octyl glucoside, oleyl alcohol, pentaethylene glycol monododecyl ether, poloxamer, poloxamer 407, polyglycerol polyricinoleate, polysorbate, polysorbate 20, polysorbate 80, saponins, sorbitan monostearate, sorbitan tristearate, stearyl alcohol, triton x-100), cationic surfactants (benzalkonium chloride, benzethonium chloride, bronidox, cetrimonium bromide, cetrimonium chloride, dimethyldioctadecylammonium chloride, lauryl methyl gluceth-10 hydroxypropyl dimonium chloride, tetramethylammonium hydroxide) and/or anionic surfactants (ammonium lauryl sulfate, dioctyl sodium sulfosuccinate, mbas assay, perfluorobutanesulfonic acid, perfluorononanoic acid, perfluorooctanesulfonic acid, perfluorooctanoic acid, potassium lauryl sulfate, saponins, soap, soap substitute, sodium dodecyl sulfate, sodium dodecylbenzenesulfonate, sodium laureth sulfate, sodium lauroyl sarcosinate, sodium myreth sulfate, sodium pareth sulfate, sodium stearate), notably surfactants adapted to facilitate rinsing of internal parts of the device to reduce contamination which could lead to parasite analysis signals over time;
- co-pigments, for example flavonoids, anthocyanins, anthocyanosides and/or cinnamic derivatives, notably chemicals that will lead to enhanced detectability of hemozoin by molecular association;
- antimicrobial agents, for example azides, benzoic acid derivatives, including hydroxyles, ethers, esters and/or salts, sorbic acid, acetic acid, sulphur derivatives, including sulphides and sulphites, nitrogen derivatives, including nitrites and nitrates, sulfamides, antibiotics, thiabendazole, notably antimicrobial agents able to suitably prevent the growth of microorganisms in the solutions;
- viscosifying, thickening or gelling agents, for example acacia gum and derivatives, acetylated mono-glycerides, acetylated tartaric acid esters of mono- and di-glycerides, agar, algin, alginic acid, ammonium alginate, ammonium carrageenan, ammonium furcelleran, ammonium salt of phosphorylated glyceride, arabinogalactan, baker's yeast glycan, calcium alginate, calcium carrageenan, carboxymethyl cellulose, carob bean gum, carrageenan, cellulose gum, gelatin, gellan gum, guar gum, gum arabic, hydroxylated lecithin, hydroxypropyl cellulose, hydroxypropyl methylcellulose, irish moss gelose, karaya gum, lactylated mono- and di-glycerides, lactylic esters of fatty acids, lecithin, locust bean gum, methylcellulose, methyl ethyl cellulose, oat gum, pectin, polyglycerol esters of fatty acids, polyglycerol esters of interesterified castor oil fatty acids, polyoxyethylene (20) sorbitan monooleate (polysorbate 80), polyoxyethylene (20) sorbitan monostearate (polysorbate 60), polyoxyethylene (20) sorbitan tristearate (polysorbate 65), polyoxyethylene (8) stearate, potassium alginate, potassium carrageenan, propylene glycol alginate, propylene glycol ether of methylcellulose, propylene glycol mono fatty acid esters, sodium alginate, sodium aluminum phosphate, sodium carboxymethyl cellulose, sodium carrageenan, sodium cellulose glycolate, sodium stearoyl-2-lactylate, sodium stearate, sodium tartrate, sodium tripolyphosphate, sorbitan monostearate, sorbitan trioleate, sorbitan tristearate, stearyl monoglyceridyl citrate, sucrose esters of fatty acids, tragacanth gum, xanthan gum, notably chemicals that will lead to enhanced viscosity of the solutions.

The magnetic separation of the target material of the sample may comprise separation in a magnetic separation column, notably a magnetic separation column containing magnetic or magnetisable particles, notably microspheres, for example steel- or iron-containing microspheres. The microspheres may have a diameter which is ≥0.3 mm or ≥0.1 mm and/or which is ≤1 mm or ≤2 mm. Such particle sizes avoid the need for fine retaining grids or filters to retain the particles within the column which would present a risk of blockage, particularly where the sample comprises a suspension.

The magnetic column may be easily disassembled and re-assembled, for example to facilitate replacement of its magnetisable particles. The magnetisable particles may be replaced periodically to maintain efficiency and/or accuracy of the device, for example in cases of corrosion and/or build-up of deposits and/or contaminants. The number of analyses conducted prior to replacing the magnetisable particles may be ≥10 or ≥15; it may be ≤1000.

The magnetic column may have an internal diameter which is ≥0.5 mm or ≥1 mm and/or which is ≤15 mm or ≤10 mm. The length of the column may be ≥5 mm or ≥1 cm and/or ≤12 cm or ≤10 cm. The column is preferably made of a non-magnetic material, for example a plastics material such as polypropylene.

An external magnetic field may be applied to the magnetic separation column, for example by one or more permanent magnets. The magnitude of a magnetic field at the separation column may be ≥0.2 T or a ≥1 T; it may be ≤8 T or ≤10 T.

The system may be configured as a microflow system. Accordingly, the size of the magnetic column, the microspheres, the magnetic field and the sample to be tested may be adapted to a microflow system. Notably in this case, the magnetic particles may be nanoparticles or nanospheres. The magnetic particles may be microspheres as described above or, preferably, lower diameter microspheres. In that case, the microspheres may have a diameter which is ≥50 μm or ≥100 μm and/or which is ≤500 μm or ≤400 μm or ≤300 μm. The magnetic column may have the form of a microbead reservoir, for example provided as part of an integrated flow cell. The integrated flow cell may comprise a microbead reservoir in fluid connection with an optical window.

The integrated flow cell may be of a size similar to a standard microscope slide. It may have dimensions of: length ≥30 mm or ≥45 mm or a ≥60 mm or ≥70 mm and/or ≤150 mm or ≤120 mm or ≤90 mm; and/or width ≥15 mm or ≥20 mm and/or ≤60 mm or ≤45 mm or ≤30 mm; and/or thickness ≥1 mm or a ≥2 mm or a ≥4 mm and/or ≤15 mm or ≤12 mm or ≤10 mm or ≤8 mm. The connecting conduits or pathways between elements of the integrated flow cell may have a diameter which is ≥20 μm or ≥50 μm and/or which is ≤200 μm or ≤150 μm. The integrated flow cell may be substantially planar; it may provide a single use device or a multi-use device, for example adapted for analysis of at least about 10 samples and/or up to about 50 samples. The flow cell may be made from a polymer, for example PMMA (poly(methyl methacrylate)) or PDMS (polydimethylsiloxane). The integrated flow cell may comprise: a first portion, for example a base, in which a flow circuit is provided, for example as a circuit open at one face, for example by being machined, engraved or moulded into a surface; and a second portion, for example a cover, which complements the base, for example by overlying the base, for example to seal an open face of the circuit provided on the first portion. A micro bead reservoir of the flow circuit may be filled with magnetisable particles, for example steel particles or nanoparticles, prior to assembly of the flow cell by positioning and sealing of the second portion over the first portion. The flow cell may be disassembled and subsequently reassembled, for example by removal of the cover, in order to replace the magnetisable microparticles.

The spectroscopic analysis of the analysable solution to detect the dissolved target material may comprise optical analysis; it may comprise absorption spectroscopy. Radiation emitted from a source may pass through the analysable solution to give an attenuated signal which is received by a sensor. The source and the sensor are chosen to encompass wavelengths at which the presence and preferably quantity of the target material can be detected.

Preferably, quasi-monochromatic light is used for the spectroscopic analysis, i.e. light having a narrow band width, for example having at least 80% of its energy within a band width of 80 nm, 50 nm, 20 nm or 10 nm. A quasi-monochromatic light source and/or sensor may be used. In one preferred embodiment, a quasi-monochromatic diode emitting at a wavelength of about 380 nm, about 405 nm or about 620 nm is used. Alternatively, monochromatic light may be used. The absorption spectrum of hemozoin shows several peaks (FIG. 1). Hemozoin absorbs radiation strongly at wavelengths in the range of 330 nm to 410 nm and to a lesser extent at wavelengths in the range of 600 nm to 640 nm. The first band is interesting for sensitivity, the second for specificity. Consequently, use of a corresponding quasi-monochromatic light source allows the use of robust, simplified arrangements and apparatus which nevertheless provides good sensitivity or selectivity. For example, the emitting diode may be a low-power diode; it may be positioned adjacent to the flow of the analysable fluid without requiring transmission by optical fibres. A particular advantage may be achieved by detection of hemozoin at about 380 nm, about 405 nm or about 620 nm using a lysed whole blood sample; this combination may be used to sensitively detect hemozoin and/or to avoid undesired or parasite signals from the sample interfering with or masking the signal indicating hemozoin. The light sensor may be a photo-sensor allowing detection at the selected wavelength. Consequently, the wavelength(s) of the spectroscopic analysis to detect the target material may comprises:

wavelengths which are ≥300 nm or ≥320 nm or ≥340 nm or ≥350 nm or ≥360 nm and/or which are ≤440 nm or ≤430 nm or ≤420 nm or ≤410 nm; or wavelengths which are ≥580 nm or ≥590 nm or ≥600 nm and/or which are ≤650 nm or ≤640 nm or ≤630 nm.

A monochromatic or quasi-monochromatic emitter centred on a wavelength within the above may be used.

The path of the radiation used in the spectroscopic analysis through the analysable solution is preferably chosen to be ≥3 mm, ≥20 mm, ≥30 mm or ≥40 mm; this helps improve sensitivity of detection. The radiation may pass along a portion of the flow path of the analysable solution, for example by arranging a "Z" portion in the flow path and passing the radiation through the longer portion of the "Z".

The method may comprise:
  a first, separation phase in which the target material is magnetically separated from the sample, for example by passing the sample through a magnetic separator and retaining the magnetic form of the target material within the separator, and/or
  a second, analysis phase in which the target material is removed from the magnetic separator, for example by dissolution and elution in a solution, so as to provide an analysable solution; and/or
  a third, rinsing phase, in which the magnetic separator is rinsed in preparation for its subsequent use.

Preferably, the spectroscopic analysis is carried out on an analysis solution which comprises the target material in solution.

The sample to be analysed may be introduced into the flow path of a carrier fluid, for example by injection, notably through an inlet, for example through an injection valve or septum. This facilitates introduction of the sample into the device without requiring interruption in its operation or disassembling.

An embodiment of the invention will now be described, by way of example only, with reference to the accompanying drawing of which:

Figure 1:
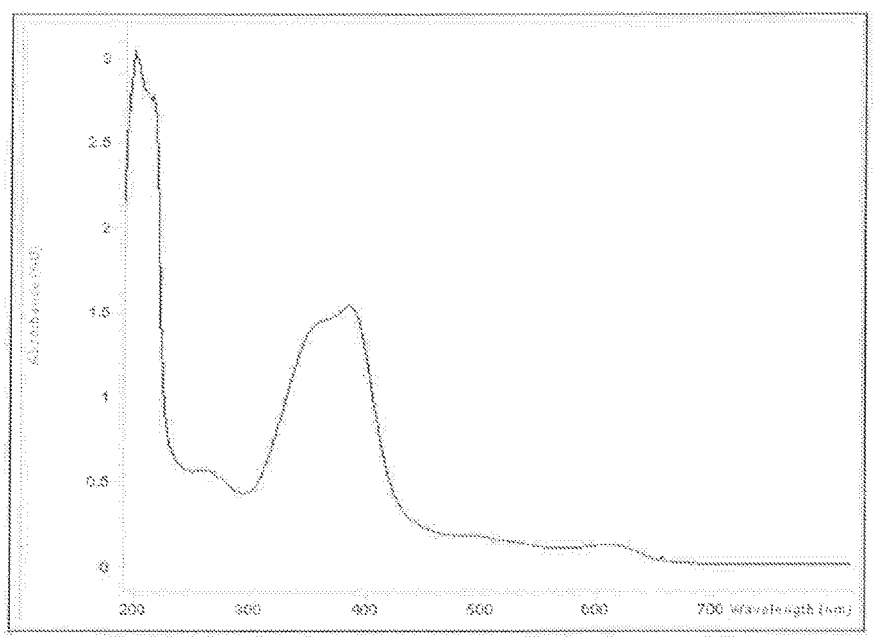
FIG. 1 is a UV-visible absorption spectrum of hemozoin
Figure 2:
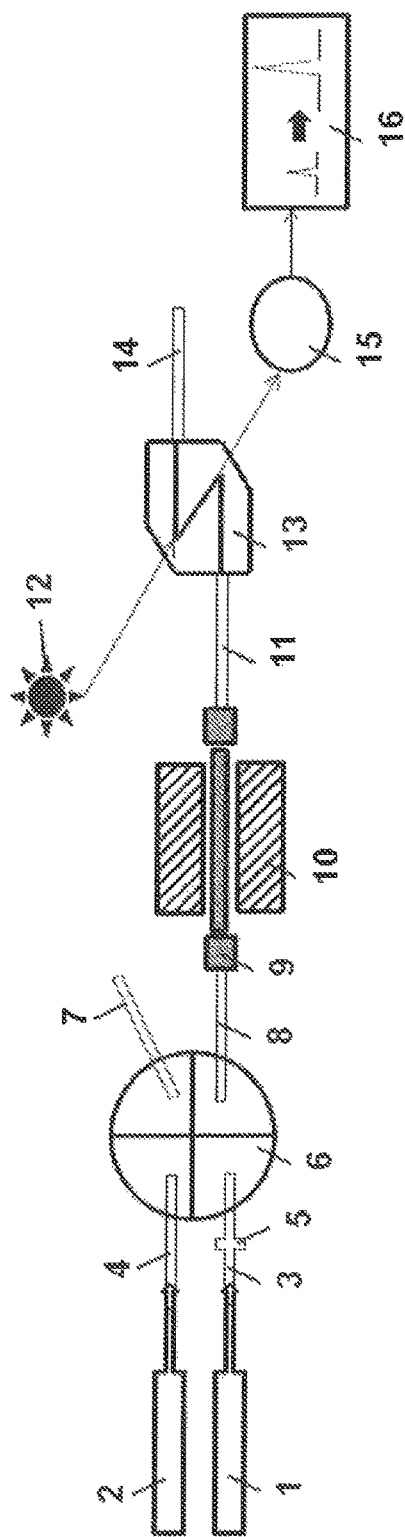
FIG. 2 is a schematic representative embodiment of an analytical device.

The analytical device of FIG. 2 comprises:

1 & 2: double syringe pump from KR Analytica fitted with first syringe 1 containing water used as a carrier fluid and second syringe 2 containing a 0.4 M sodium hydroxide (NaOH) solution used as a collecting, dissolving and eluting fluid, the syringe pump being set to create from each of the syringes a constant flow of 0.5 mL/min;

3: connecting tube between syringe 1 and a switch valve;
4: connecting tube between syringe 2 and the switch valve;
5: entry septum to inject the sample;
6: switch valve from Rheodyne TitanMX;
7: connecting tube from the switch valve to disposal;
8: connecting tube between the switch valve and the column;
9: magnetic separation column comprising a polypropylene column having a length of about 60 mm and an internal diameter of about 4 mm containing about 4 g of steel microspheres having a diameter of about 0.5 mm);
10: permanent magnets (MidiMACS magnets from Miltenyi Biotec) generating a magnetic field having a magnitude of about 0.65 T;
11: connecting tube between the column and the flow cell;
12: quasi-monochromatic light-emitting diode (405 nm) used as a light source;
13: flow cell ("SMA Z-cell" from Ocean Optics including UV-Vis silica windows for wavelengths higher than 210 nm);
14: connecting tube from the flow cell to disposal;
15: light sensor;
16: signal amplifier and voltmeter Synthesis of β-hematin was carried out in accordance with an adapted method described in "An iron-carboxylate bond links the heme units of malaria pigment" (AFG Slater et al, 1991, Proc. Natl. Acad. Sci. USA, Vol. 88, pp. 325-329). A stock solution of a 45.4 mM of hematin was prepared from dissolving 0.592 g of hemin porcine with a 0.4 N sodium hydroxide (NaOH) solution to obtain 20 mL solution of the said solution. 10 mL of the stock solution were diluted with 90 mL of water to obtain 100 mL of a 4.54 mM solution of hematin, thereafter 2% propionic acid was added to obtain a reaction medium with a pH of 4. In a closed recipient the mixture is allowed to react at 70° C. in a thermostated bath during 18 h before being filtered. The residue from filtration was collected and dried in an oven at 37° C. during 24 h. The β-hematin crystals are then kept in fridge at 4° C.

In order to simulate the detection of malaria (hemozoin crystals) in a human whole blood sample, a sample to be tested was made up as a suspension of β-hematin in a non-contaminated whole blood sample. Prior to its analysis the whole blood sample was lysed with a Tris-buffered (pH 7), Triton X-100 and saponin solution. The lysis solution was prepared following a protocol adapted from a method described in "Simple and Inexpensive Fluorescence-Based Technique for High-Throughput Antimalarial Drug Screening" (M. Smikstein et al., Antimicrob. Agents Chemother., 2004, vol. 48, p 1803). Firstly 100 mL of a Tris-buffered solution was prepared. After dissolving 12.11 g of Tris (hydroxymethyl)aminomethane in 60 mL of water and adding HCl (hydrochloric acid) to obtain a solution with a pH of 7, water was subsequently added to obtain 100 mL of the Tris-buffered solution. 100 mL of the lysis solution was obtained by adding the necessary volume of Tris-buffered solution to 10 mg of saponin and 1 mL of Triton X-100. This lysis solution was kept in fridge at 4° C. and used within 7 days. The lysate of the whole blood sample was performed by a ½ dilution with the lysis solution and a reaction time of 30 minutes.

At the start of a first separation phase, the device is stabilised with the switch valve (6) set so that the carrier fluid from syringe (1) is directed to the flow path through the magnetic column (9) and the collecting fluid from syringe (2) is sent from the switch valve (6) to disposal.

300 µL of a lysed whole blood sample containing β-hematin crystals are injected into the septum (5). As the sample is a suspension it should be shaken just before injection to ensure that the injected sample is homogeneous. During this first phase, lasting about 2½ minutes, the water from the syringe (1) passes through the connecting tube (3) and carries the injected sample through the switch valve (6) and through the connecting tube (8) to the inlet of the magnetic column. As the sample transported by the carrier fluid passes over the magnetised steel microspheres in the column, the magnetic β-hematin crystals in the sample are attracted to and retained by the magnetised microspheres.

At the end of the separation phase, the device is switched in to a second analysis phase, which has a duration of about 2½ minutes. In the analysis phase, the switch valve (6) is commuted so that the carrier fluid from the syringe (1) is sent from the switch (6) to disposal and the collection solution from the syringe (2) is directed by the switch (6) through the connecting tube (8) to the inlet of the separation column (9). The collecting solution is selected so that, as it passes over the microspheres, it collects and elutes the β-hematin crystals retained by the microspheres during the separation phase to provide an analysable solution which, in this embodiment, comprises the β-hematin crystals dissolved in the sodium hydroxide collecting solution.

The outlet of the separation column is connected via a connecting tube (11) to a flow cell (13) where an emitted light from a narrow bandwidth diode (centred on 405 nm) passes through the analysable solution and the attenuated transmitted light signal falls on a light sensor (15). The light absorption detected in the attenuated light signal provides an indication of the presence and quantity of the dissolved β-hematin or hemozoin crystals from the sample. An output of the light sensor (15) is connected to a signal amplifier and voltmeter (16) and subsequently connected to a computer configured to process and display the signal.

The fluid outlet from the flow cell (13) is sent through a connecting tube (14) to disposal.

At the end of the analysis phase the device is switched to a third, rinsing phase during which the switch valve (6) directs the collecting fluid from syringe (2) to disposal and directs the carrier fluid from syringe through the connecting tube (8) to the separation column (9).

Figure 3:
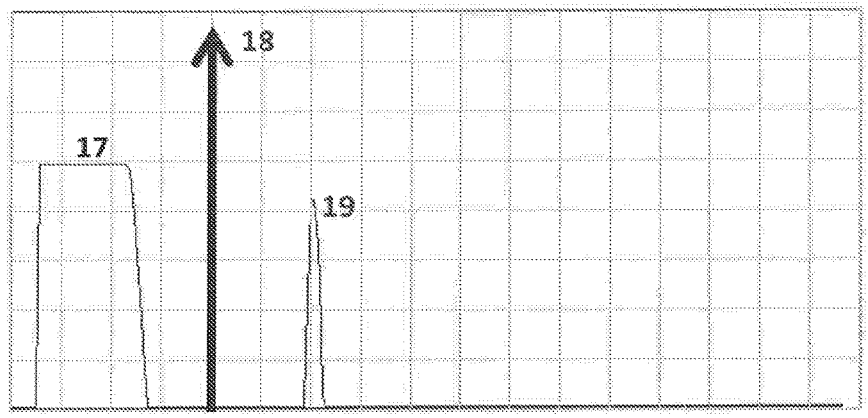
FIG. 3 is a chromatogram obtained via the program PcLab2000 from a sample of lysed whole blood containing β-hematin.

FIG. 3 is a chromatogram obtained via the program PcLab2000 from a sample of lysed whole blood containing 1-hematin showing signal amplitude (in volts on the y axis) as a function of time (in seconds on the x axis). Arrow (18) indicates when the switch valve commutes to pass from the separation phase to the analysis phase. Peak (19) corresponds to detection of S-hematin in the analysis solution. The surface area of this peak (19) is correlated to the concentration of β-hematin in the sample.

Figure 4:
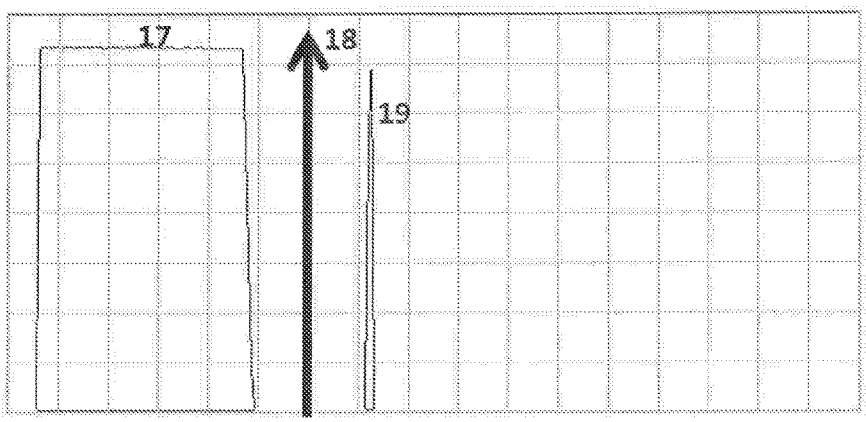
FIG. 4 is a chromatogram obtained via the program PcLab2000 from a sample of malaria-contaminated lysed whole blood.

FIG. 4 is a chromatogram obtained via the program PcLab2000 from a sample of lysed malaria-contaminated whole blood sample analysed using the procedure described above.

To determine the quantity of hemozoin (or β-hematin) in the sample, a preliminary calibration curve may be made, notably using calibration samples containing known quantities of β-hematin. For example, the calibration curve indicates the concentration of hemozoin as a function of surface area under the peak signal corresponding to the hemozoin (which may be determined using Graph Pad software) or, in a simplified but less accurate alternative, as a function of the maximum intensity of the peak signal corresponding to the hemozoin in the absorption signal.

The simplicity and robustness of the device facilitate its use in field situations. The rapidity of obtaining a reliable result with a high level of sensitivity which is not significantly dependent upon the skill of the operator is also advantageous.

Figure 5:
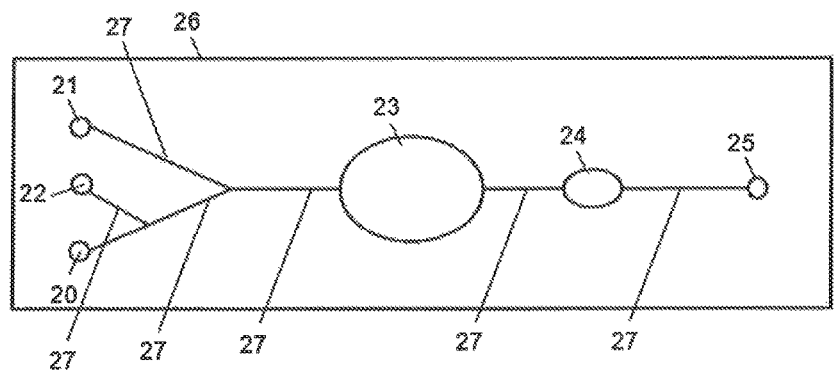
FIG. 5 is a schematic plan view of a microfluidic system in the form of an integrated flow cell.

FIG. 5 is a schematic representation of a microflow system in the form of an integrated flow cell 26 having a length of 76 mm and a width of 26 mm which comprises:
20: an inlet for the carrier fluid
21: an inlet for the collecting fluid
22: an inlet for the sample
23: a micro-bead reservoir
24: an optical window
25: an outlet/disposal
and which comprises the micro-bead reservoir and the optical window in the form of a planar flow cell or chip. The planar flow cell is adapted for use with at least (i) its micro-bead reservoir either laid over a permanent magnet or sandwiched between a pair of planar permanent magnets; and (ii) with a light emitter and light sensor arranged at the optical window. The geometry of magnets and their positioning may be modified to ensure a suitable magnetic field. The connecting passages or conduits 27 leading a) from the inlets of the carrier fluid, the collecting fluid and the sample to an inlet of the micro-bead reservoir b) from an outlet of the micro-bead reservoir to an inlet of the optical window and c) from an outlet of the optical window to the outlet/disposal; have a diameter of 100 μm. The micro-bead reservoir contains magnetisable steel microparticles having a diameter of 200 μm.

The carrier fluid and the collecting fluid are provided from external containers and are pumped through the flow cell, for example using a peristatic pump for each fluid. The use of peristatic pumps which comprise non-return valves avoids the need for continuous fluid circulation and a switch valve (6) with an intermediate disposal (7) such as described for the analytical device of FIG. 2. The sample to be analysed may be introduced via a micropipette, for example an Eppendorf® micropipette, or a glass capillary.

The device may be provided as a kit comprising: one or more flow cells 26 filled with the magnetic microparticles, external magnet(s), notably permanent magnets, peristatic pumps, a light emitter and associated light sensor, signal processing equipment and an interface screen for presenting the results, preferentially a touch-screen interface.

The microflow system provides a particularly compact, low cost, rapid analysis system suitable for field use with small sample volumes.

The invention claimed is:

1. A method of detecting a target material in a sample comprising the target material in a form having magnetic properties, the method comprising:
   magnetic separation of the magnetic form of the target material from the sample in a first phase in which the target material is magnetically separated from the sample by passing the sample through a magnetic separator and retaining the magnetic form of the target material within the separator;
   dissolution of the separated magnetic form of the target material to provide an analysable solution comprising the target material in a second phase in which the target material is removed from the magnetic separator by dissolution and elution in a solution, notably in an un-magnetised form, so as to provide the analysable solution; and
   spectroscopic analysis of the analysable solution to detect the target material.

2. The method according to claim 1, wherein the target material comprises hemozoin or hematin.

3. The method in accordance with claim 2, wherein the method comprises a method of detection and quantification of hemozoin in a blood sample to detect malaria infection and/or to estimate and/or quantify parasitemia.

4. The method in accordance with claim 3, wherein the sample comprises a lysed whole blood sample.

5. The method in accordance with claim 1, wherein the magnetic separation of the magnetic form of the target material from the sample comprises applying a magnetic field having an intensity in the range of 0.2 to 10 T.

6. The method in accordance with claim 1, wherein the magnetic separation of the magnetic form of the target material from the sample comprises passing the sample over magnetic particles, notably magnetised iron-containing particles, in a magnetic separation column.

7. The method in accordance with claim 1, wherein the dissolution of the separated magnetic form of the target material to provide an analysable solution comprises dissolution in an aqueous solution comprising an alkalinizing agent selected from the group consisting of calcium hydroxide, magnesium hydroxide, sodium hydroxide, ammonium hydroxide, organic quaternary ammonium hydroxides, ammonia, organic amines and combinations thereof.

8. The method in accordance with claim 1, wherein the spectroscopic analysis comprises optical absorption spectroscopy, wherein light emitted from a light source passes through the analysable solution to give an attenuated transmitted light which is received by a light sensor.

9. The method in accordance with claim 8, wherein an indication of the amount of target material in the sample is obtained through the absorbance of the transmitted light.

10. The method in accordance with claim 1, wherein the spectroscopic analysis of the analysable solution to detect the dissolved magnetic target material comprises analysis of a quasi-monochromatic light, notably comprising wavelengths in the range 350 nm to 420 nm or 600 to 640 nm.

11. The method in accordance with claim 1, wherein the target material having magnetic properties comprises hemozoin and the method is capable of detecting a concentration of hemozoin in the sample which is less than 0.1 μg/mL, preferably less than 0.08 μg/mL.

12. A device for detecting the presence of a target material in a liquid sample comprising the target material in a form having magnetic properties, the device comprising:
- a magnetic separator having a sample flow path between a sample inlet and a sample outlet, the magnetic separator flow path passing over magnetic members, notably magnetisable microspheres, retained within the magnetic separator; and
- a spectroscopic analyser having a sample flow path between a sample inlet and a sample outlet, the sample outlet of the magnetic separator being in fluid connection with the sample inlet of the spectroscopic analyser, the spectroscopic analyser flow path comprising a detection zone and the spectroscopic analyser comprising a radiation emitter, notably a quasi-monochromatic light emitter, configured to emit radiation in to the detection zone and a sensor configured to detect radiation at the detection zone.

13. The device in accordance with claim 12, wherein the device further comprises one or more of: a septum inlet allowing introduction of a sample into a flowpath of a carrier fluid; a source, notably a syringe, adapted to introduce a carrier fluid into the magnetic separator; a source, notably a syringe, adapted to introduce a collecting and/or dissolving fluid into the magnetic separator; a fluid flow device, notably a pump, adapted to create a flow of a fluid through the device; a radiation source, notably a quasi-monochromatic light source, adapted to emit radiation through a flowpath of the sample to be analysed; a sensor adapted to detect radiation that has passed through the flowpath of the sample to be analysed; signal processing equipment adapted to provide an indication of the presence and/or quantity of the target material in the sample on the basis of an output from the spectroscopic analyser.

14. The device in accordance with 12, wherein the device is connected to signal analyser configured to provide an indication of the quantity of target material in the sample on the basis of an output signal from the spectroscopic analyser.

\* \* \* \* \*